(12) United States Patent
Ristimäki et al.

(10) Patent No.: US 6,416,961 B1
(45) Date of Patent: Jul. 9, 2002

(54) DIAGNOSIS OF EARLY GASTRIC CANCER

(75) Inventors: Ari Ristimäki, Helsinki; Matti Härkönen; Pentti Sipponen, both of Espoo, all of (FI)

(73) Assignee: Biohit Oyj, Helsinki (FI)

( * ) Notice: Subject to any disclaimer, the term of this patent is extended or adjusted under 35 U.S.C. 154(b) by 0 days.

(21) Appl. No.: 09/381,042

(22) PCT Filed: Mar. 18, 1998

(86) PCT No.: PCT/FI99/00238
§ 371 (c)(1),
(2), (4) Date: Sep. 14, 1999

(87) PCT Pub. No.: WO98/41864
PCT Pub. Date: Sep. 24, 1998

(30) Foreign Application Priority Data

Mar. 18, 1997 (FI) .................................................. 971124

(51) Int. Cl.⁷ .............................................. G01M 33/53
(52) U.S. Cl. ........................... 435/7.23; 435/6; 435/7.1; 530/387.1; 530/388.1; 530/350
(58) Field of Search ............................ 435/7.1, 6, 7.23; 530/387.1, 388.1, 350

(56) References Cited

FOREIGN PATENT DOCUMENTS

CA          2140091          7/1995

OTHER PUBLICATIONS

Lam, S K. Annals Academy Med; Singapore, 28(6): 881–9, 1999.*
Cahill. Gut, 38: 177–181, 1996.*
Tockman, S et al. Cancer Res. 52: 2711S–2718S, 1992.*
Tsuji et al, Prostaglandine Leukotrienes and Essential Fatty Acids, vol. 55, No. 3, 1996, pp. 179–183.
Williams et al, Gastroenterology, vol. 111, 1996, pp. 1134–1140.
Ristimaki A. et al, Dialog Information Services, File 34, Scisearch, Dialog accession No. 05690158, 1997, Abstract.

* cited by examiner

Primary Examiner—Anthony C. Caputa
Assistant Examiner—Minh-Tam Davis
(74) Attorney, Agent, or Firm—Birch, Stewart, Kolasch & Birch, LLP (57) ABSTRACT

The present invention pertains to a method for determination of the significance of a histologically detected premalignant lesion as a risk for intestinal type gastric cancer or carcinoma in situ, comprising detecting from a patient sample comprising gastric mucosa cells a) cyclooxygenase-2 Cox-2) mRNA expression, or
b) Cox-2 protein;

wherein overexpression of Cox-2 is indicative of an increased risk for intestinal type gastric cancer.

7 Claims, 5 Drawing Sheets

DIAGNOSIS OF EARLY GASTRIC CANCER

This application is the national phase under 35 U.S.C. §371 of PCT International Application No. PCT/FI98/00238 which has an International filing date of Mar. 18, 1998 which designated the United States of America. This application also claims priority under 35 U.S.C. §119(a)–(d) of prior foreign application Finland No. 971124 which has a filing date of Mar. 18, 1997.

FIELD OF THE INVENTION

The present invention relates to diagnosis of stomach cancer and concerns in specific a method for detection of gastric carcinoma at a premalignant phase by detecting cyclooxygenase-2 expression in a patient sample.

BACKGROUND OF THE INVENTION

Gastric cancer is one of the most frequent and lethal malignancies in the world (Coleman et al., 1993). It is the fourth most common malignancy in Finnish males and the fifth in females, and accounts for 5% of all malignancies in Finland (Cancer Incidence in Finland 1994. Finnish Cancer Registry, Helsinki, 1996). Early detection of stomach cancer is difficult, and in most western countries the five year survival rate is less than 20% (Wanebo et al., 1993). More than 90% of stomach cancers are adenocarcinomas, which are divided into intestinal and diffuse types by the Lauren classification (Lauren, 1965).

Pathogenesis of gastric cancer is complex and incompletely understood, but in the case of intestinal type certain precursor changes, such as chronic atrophic gastritis, intestinal metaplasia, and epithelial dysplasia, have been associated with the disease (Antonioli, 1994). In contrast, the diffuse type lacks well-recognized precursor lesions. Since a different combination of genetic changes have been found in these two histologically distinct types of gastric cancer, they may possess different genetic backgrounds (Stemmermann et al., 1994; Tahara et al., 1996). However, malignancy related genetic changes shared by these two gastric adenocarcinoma types are thought to represent those that appear already at the premalignant phase of the disease (Tahara et al., 1996), Nonsteroidal anti-inflammatory drugs (NSAIDs), such as aspirin, indomethacin, and sulindac, inhibit chemically induced carcinoma of the colon in animal models (Steele et al., 1994; Giardiello et al., 1995). Epidemiological studies have shown that prolonged use of aspirin decreases incidence of and mortality from gastrointestinal cancers, including stomach cancer (Laakso et al., 1986; Giardiello, 1994; Thun, 1994; Thun et al., 1993).

The best known target of NSAIDs is cyclooxygenase (Cox), the rate-limiting enzyme in the conversion of arachidonic acid to prostanoids. Two Cox genes have been cloned (Cox-1 and Cox-2) that share over 60% identity at amino acid level and have similar enzymatic activities (Hershman, 1996; Smith et al., 1996). Cox-1 is considered as a housekeeping gene, and prostanoids synthesized via the Cox-1 pathway are thought to be responsible for cytoprotection of the stomach, for vasodilatation in the kidney, and for production of a proaggregatory prostanoid, thromboxane, by the platelets. In contrast, Cox-2 is an inducible immediate-early gene, and its pathophysiological role has been connected to inflammation, reproduction, and carcinogenesis.

Recent studies suggest that Cox-2 is connected to colon carcinogenesis and may thus be the target for the chemopreventive effect of NSAIDs: i) genetic disruption of Cox-2 gene or treatment with a Cox-2 specific drug suppress the polyp formation in a mice model for FAP (Oshima et al., 1996), ii) overexpression of Cox-2 in rat intestinal epithelial cells alters their rate of programmed cell death and their adhesion to the extracellular matrix (Tsujii et al., 1995), and iii) two different Cox-2-selective inhibitors suppress chemically induced aberrant crypt foci in the rat colon (Takahashi et al., 1996; Reddy et al., 1996). Further, elevated levels of Cox-2 mRNA and protein, but not those of Cox-1, are found in chemically induced rat colon carcinoma tissues (DuBois et al., 1996) and in human colon carcinoma, when compared to normal mucosa (Eberhart et al., 1994; Kargman et al., 1995; Sano et al., 1995).

The idea that chemopreventive effect of NSAIDs would be targeted against Cox-2, is further supported by the findings that Cox-2 selective compounds inhibit proliferation of rat intestinal epithelial cells, and mammary epithelial cells wherein Cox-2 expression was induced by oncogenes (Sheng et al., 1997 and Subbaramaiah et al. 1996). Also, Tsuji et al. (1996) reported recently that a Cox-2 specific inhibitor suppressed proliferation of a gastric and a colon carcinoma cell line, which expressed high steady-state levels of Cox-2 mRNA. This was not the case in cell lines that express low levels of Cox-2 mRNA.

Normal gastrointestinal tissues contain almost exclusively the Cox-1 isoform, and no functional Cox-2 protein was found in healthy stomach tissue (Kargman et al., 1996). Some Cox-2 mRNA may, however, be detected with more sensitive methods than the traditional Northern blot hybridization assay of total RNA, e.g. with RT-PCR (see O'Neill and Ford-Hutchinson 1993, and FIGS. 2 and 4 in the present work).

DESCRIPTION OF THE INVENTION

Since it is not known, whether Cox-2 is present in gastric cancer tissues in vivo, or in premalignant lesions of gastric carcinoma, we studied its expression in adenocarcinomas of the stomach, as well as in grave gastric dysplasias (which are highly premalignant). We found elevated levels of Cox-2 mRNA, but not those of Cox-1, in human gastric adenocarcinoma tissues and grave dysplasias of the stomach. However, the expression of Cox-2 was not elevated in mild dysplasias that rarely transform to malignancies. In gastric carcinoma, Cox-2 protein was primarily localized in the cancer cells.

Elevated expression of Cox-2 was not limited to the intestinal type, since each of the three diffuse carcinomas analysed contained higher levels of Cox-2 mRNA than their respective controls. Thus, overexpression of Cox-2 is one of the properties shared by these two histologically and genetically distinct diseases, which may suggest that it is involved with the early phase of carcinogenesis. Indeed, we found that Cox-2 is expressed in grave dysplasias of the stomach, whereas the expression was not elevated in mild dysplasias. This suggests that Cox-2 expression may be specifically associated with the premalignant lesions of gastric carcinoma.

In conclusion, we have shown that Cox-2 is expressed in human gastric carcinoma tissues, when compared to paired gastric mucosal specimens devoid of cancer cells. Cox-2 mRNA was found both in intestinal and diffuse adenocarcinomas. Cox-2 protein is localized to gastric carcinoma cells, but not to the surrounding stroma, as detected by immunohistochemistry. Importantly, grave gastric dysplasia specimens that represent premalignant lesions are strongly Cox-2 positive. This suggests that Cox-2 may be used as diagnostic marker of early gastric carcinoma, and in determination of the severity of premalignant lesions.

Expression of Cox-2 in human carcinomas seems, at least so far, to be restricted to the gastrointestinal tract. However, as colon carcinoma and stomach carcinoma are both epidemiologically, morphologically and genetically distinct diseases, the fact that elevated levels of Cox-2 mRNA and protein have been found in rodent and in human colon carcinoma tissues, does not give any indication of their role in gastric tissues. The fact that one gastric carcinoma cell line was shown to express high steady-state levels of Cox-2 mRNA, is neither any indication of its role in early gastric cancer in vivo.

The objective of this invention is to develop a method for diagnosis of early gastric carcinoma, which method comprises detection of Cox-2 mRNA or the Cox-2 protein in relevant patient samples. This is based on our finding that Cox-2 is highly expressed in gastric carcinoma cells and in premalignant lesions, but that its expression is very low or undetectable in normal stomach tissues.

The patient samples to be detected are e.g. biopsies or brush samples, which are obtained during routine gastroscopy or gastric lavage combined with brush technique. Gastric lavage and brush technique are well known methods in routine gastric cytology. These techniques provide cell samples from gastric mucosa for microscopic examination to include or exclude the possibility of malignancies in the stomach. Markers, such as Cox-2, may increase the sensitivity and specialty of the assay, when compared to the present method of just visualizing the morphology of the cells. Gastroscopic biopsy samples are either formalin fixed (for immunohistochemistry) or frozen in liquid nitrogen and stored in −70° C. (for mRNA assays).

Cox-2 mRNA can be conveniently detected from said patient samples using methods known in the art. For instance, Northern blot analysis was shown by us to be extremely specific, and when combined to RT-PCR also very sensitive.

Cox-2 protein detection can be conveniently carried out from said patient samples using e.g. immunohistochemistry, which in addition to detection of Cox-2 expression shows the localization of the protein.

The present invention also provides test kits for carrying out the diagnostic method of the invention. Thus a kit for detection of Cox-2 mRNA expression comprises RNA or poly-A+mRNA isolation reagents, Cox-2 specific primers for RT-PCR and cDNA fragments for making either DNA or RNA (both sense and antisense) probes.

A kit for immunological detection of the Cox-2 protein comprises Cox-2 specific polyclonal or monoclonal antibodies. For peptide based analysis of Cox-2 protein a diagnostic kit is designed which comprises specific peptides with binding affinity to Cox-2. Such peptides are obtainable e.g. from phage display libraries. Also oligonucleotide based assays can be used, whereby oligonucleotides (modified RNA molecules) are included in a corresponding diagnostic kit.

BRIEF DESCRIPTION OF THE DRAWINGS

FIG. 4C. The graph shows the ratio of Cox-2 mRNA to GAPDH mRNA. There was no statistical difference between mild dysplasia (Dysplasia I) samples (453±125, mean±SEM) and their respective controls (424±90).

EXPERIMENTAL

| Abbreviations | |
| --- | --- |
| RT-PCR | Reverse Transcriptase-Polymerase Chain Reaction |
| Cox-1 | Cyclooxygenase 1 |
| Cox-2 | Cyclooxygenase 2 |
| NSAID | Nonsteroidal antiinflammatory drug |
| FAP | Familial adenomatous polyposis |
| mRNA | messenger RNA (ribonucleic acid) |
| GAPDH | glyceraldehyde-3-phosphate dehydrogenase |
| SDS | sodium dodecyl sulfate |

Patient Samples. Twelve gastric adenocarcinoma (Table 1) and twelve ovarian carcinoma specimens of mucinous histology were obtained from surgically removed tissues that were frozen in liquid nitrogen, and stored at −70° C. until analysed. One case of gastric carcinoma, because it showed strong autolysis in histological examination, was excluded from analysis. In the case of gastric carcinoma, paired samples of gastric mucosa, which contained no macroscopic tumor tissue or histologically detectable cancer cells were obtained from antrum (n=10) and corpus (n=10). All stomach cancers were primary adenocarcinomas, of which eight were intestinal and three of diffuse type (Lauren, 1965) as evaluated by the same pathologist.

TABLE 1

Characterization of 11 gastric carcinoma cases.

| Case | Age (yr) | Sex | Cancer site | Cancer type | Cancer %[a] | Antrum sample[b] | Corpus sample[b] |
|---|---|---|---|---|---|---|---|
| 1 | 88 | male | angulus | intestinal | 50 | mild | mild |
| 2 | 82 | male | corpus | intestinal | 100 | (no sample) | moderate[c] |
| 3 | 69 | male | antrum | intestinal | 20 | severe | mild |
| 4 | 67 | male | whole stomach | diffuse | 30 | mild | (no sample) |
| 5 | 66 | male | antrum, pylorus | intestinal | 50 | mild | not present |
| 6 | 70 | female | angulus | intestinal | 40 | moderate | not present |
| 7 | 85 | male | pylorus | intestinal | 80 | mild | mild |
| 8 | 75 | male | antrum | diffuse | 90 | not present | mild |
| 9 | 62 | male | corpus | intestinal | 60 | not present | severe |
| 10 | 82 | male | angulus | intestinal | 60 | mild | mild |
| 11 | 73 | male | antrum, prepylorus | diffuse | 30 | not present | not present |

[a]Percentage of tumor cells in the gastric carcinoma samples.
[b]Severity of atrophic gastritis and intestinal metaplasia in specimens containing no cancer cells.
[c]Yield of RNA was insufficient for Northern blot analysis.

RNA Isolation and Northern Blot Analysis. Total RNA was isolated by the method of Chomczynski and Sacchi (1987) with RNAzol™ B reagent (Tel-Test, Friendswood, Tex.) and quantitated by absorbance at 260 nm. RNA samples (15 µg) were denatured in 1 M glyoxal, 50% dimethylsulfoxide, and 10 mM phosphate buffer at 50° C. for 60 min, electrophoresed through an 1.2% agarose gel, and transferred to Hybond-N nylon membranes (Amersham International, Aulesbury, UK), which were then UV irradiated for 6 min with a Reprostar II UV illuminator (Camag, Muttenz, Switzerland). Purified cDNA fragments of human Cox-1 ORF (1.8 kb), Cox-2 ORF (1.8 kb), and glyceraldehyde-3-phosphate dehydrogenase (GAPDH, 0.8 kb) were labeled with [$^{32}$P]-α-dCTP (3000 Ci/mmol, DuPont, New England Nuclear, Boston, Mass.) and the Prime-a-Gene kit (Promega, Madison, Wis.). Probes were purified with nick columns (Pharmacia, Uppsala, Sweden) and used at 1×10$^6$ cpm/ml in hybridization solution containing 50% formamide, 6×SSC (1 x SSC=0.15 M NaCl and 0.015 M Na citrate, pH 7.0), 0.1% Ficoll, 0.1% polyvinylpyrrolidone, 0.1% bovine serum albumin, 100 µg/ml herring sperm DNA, 100 µg/ml yeast RNA, and 0.5% sodium dodecyl sulfate (SDS) at 42° C. for 16 h. Filters were washed three times with 0.1–1×SSC and 0.1% SDS at 50° C. Northern blots were quantitated with Fujifilm IP-Reader Bio-Imaging Analyzer BAS 1500 (Fuji Photo Co., Tokyo, Japan) and the MacBas software supplied by the manufacturer and visualized by autoradiography.

Reverse Transcriptase-Polymerase Chain Reaction (RT-PCR). Total RNA (1 µg) was converted to cDNA with Superscript II (Life Technologies, Gaithersburg, Md.) with both oligo-dT (Pharmacia) and random hexamers (Life Technologies). To obtain semi-quantitative results, three parameters were optimized: number of cycles, concentration of primers, and annealing temperature. The cDNA (4 µl) was PCR amplified in 100 µl reaction mixture that contained 10 mM Tris-HCl, pH 8.8, 50 mM KCl, 0.2 mM dNTPs, 1.5 mM MgCl, 0.2 µg (Cox-1) or 2 µg (Cox-2) of sense and antisense primers (Ristimäki et al., 1994), and 2.5 U of Dynazyme II DNA Polymerase (Finnzymes, Espoo, Finland). For the experiment of FIG. 2 the samples were amplified for 30 (Cox-1) or 32 (Cox-2) cycles of denaturation at 96° C. for 1 min, annealed at 60° C. (Cox-1) or 46° C. (Cox-2) for 1 min, and extended at 72° C. for 1 min. Amplified cDNAs were analyzed by 2% agarose gel electrophoresis and ethidium bromide staining. The amplified products were quantitated with a high performance CCD camera (Cohu 4910 series with on chip integration, Cohu Inc., San Diego, Calif.) and with Scion Image 1.57 software (Scion Corp., Frederick, Md.) on a Macintosh personal computer.

Figure 4A:
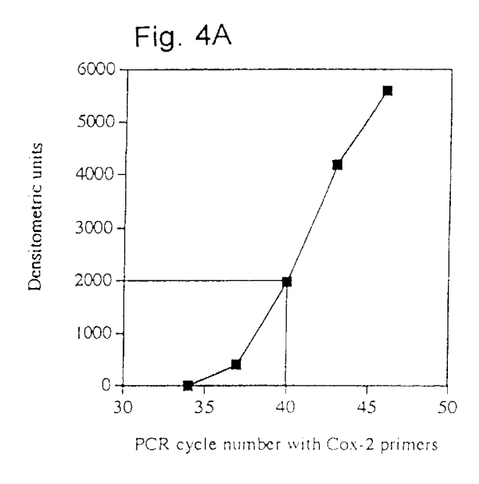
FIG. 4A. Cox-2 mRNA levels were detected by RT-PCR in gastric specimens with mild dysplasia and from their respective controls that were devoid of dysplasia. Procedure: see FIG. 2. The graph shows PCR cycle titration of Cox-2. The cycle number 40 was used in the FIG. 4C.
Figure 4B:
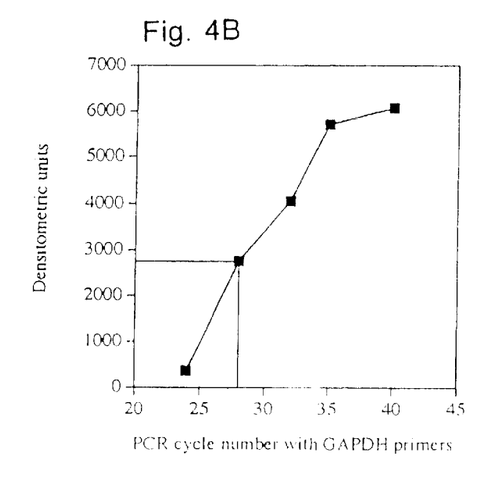
FIG. 4B. The graph shows PCR cycle titration of GAPDH. The cycle number 28 was used in the FIG. 4C.
Figure 4C:
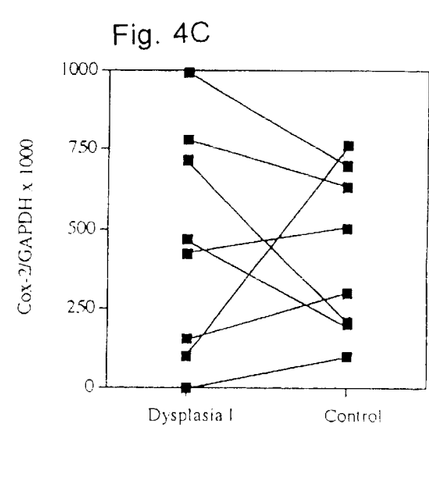

The RT-PCR procedure for the FIG. 4A and FIG. 4B was carried out as described above. However, the cycles indicated were retitrated; the results are given in FIG. 4C.

Immunohistochemistry. Tissue samples were fixed in 10% neutral-buffered formalin, embedded in paraffin, sectioned (appr. 5 µm), deparaffinized and microwaved for 15 min in 0.1 M Na-citrate buffer (pH 6.0). The slides were then immersed in 0.6% hydrogen peroxide for 30 min and after that in normal goat serum (5%)/bovine serum albumin (10%) for 1 h to block endogenous peroxidase activity and unspecific binding sites, respectively. Immunostaining was performed with a rabbit polyclonal immunoglobulin G against a mouse Cox-2 peptide (Cayman Chemical Co., Ann Arbor, Mich.) in a dilution of 1:300–1:600 at 4° C. overnight. The sections were thereafter treated with biotinylated secondary antibodies in a dilution of 1:200 (Vector Laboratories, Burlingame, Calif.) and antibody binding sites were finally visualized by avidin-biotin peroxidase complex solution (ABComplex, Vectastain, Vector Laboratories) and 3-amino-9-ethylcarbazole (Sigma Chemical Co., St. Louis, Mo.). The counterstaining was performed with Mayer's hemalaum (Merck, Darmstadt, Germany).

Statistical analysis. Statistical significance was calculated with the Wilcoxon Signed Rank test, and P<0.05 was selected as the statistically significant value. All results are shown as means±SEM.

RESULTS

Figure 1A:
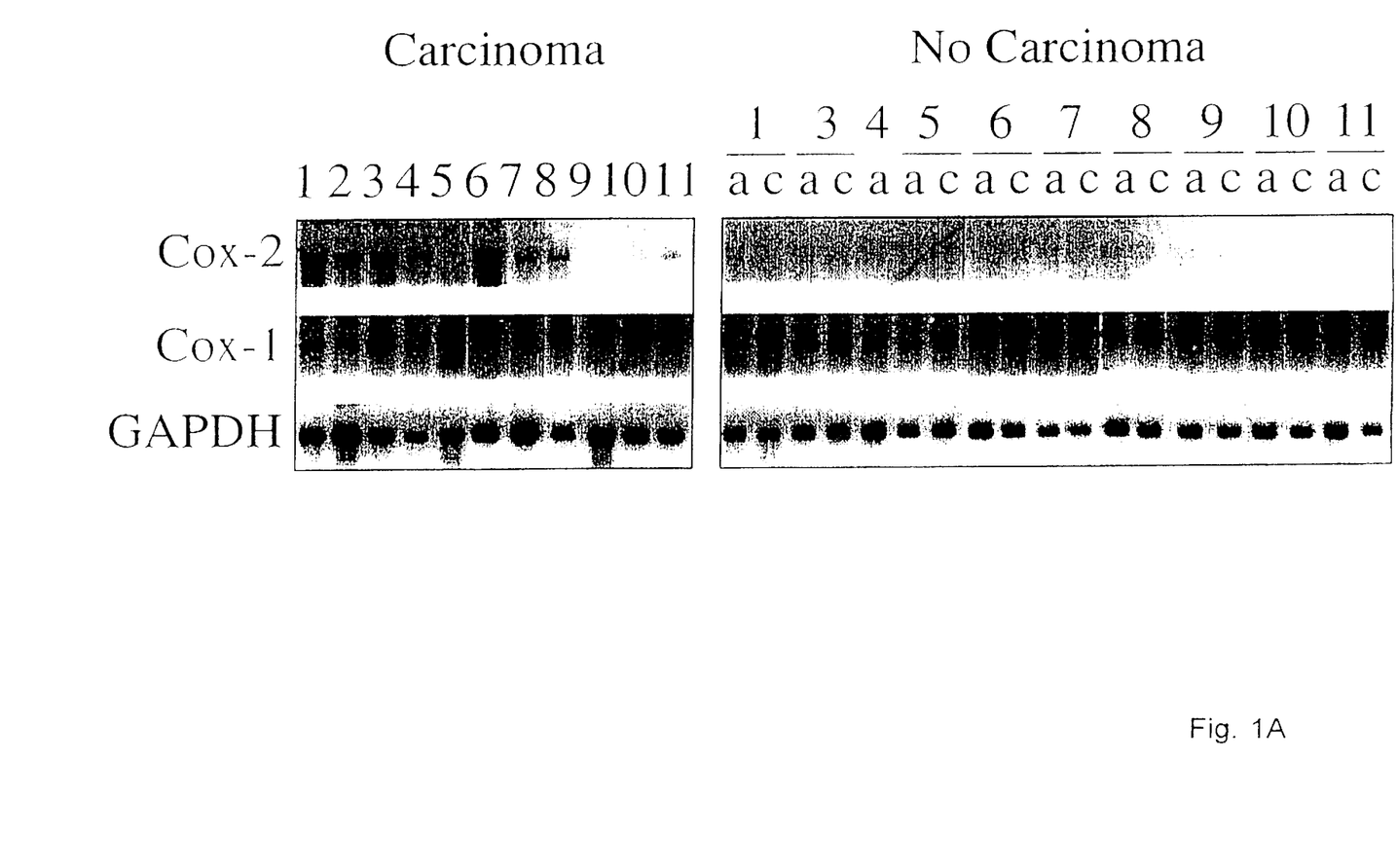
FIG. 1A. Northern blot hybridization analysis of total RNA extracted from gastric carcinoma specimens 1–11 and from their paired control samples that contained no cancer cells (a, antrum; c, corpus). Hybridization was performed with probes for human Cox-1 and Cox-2 and with GAPDH as the loading control.
Figure 1B:
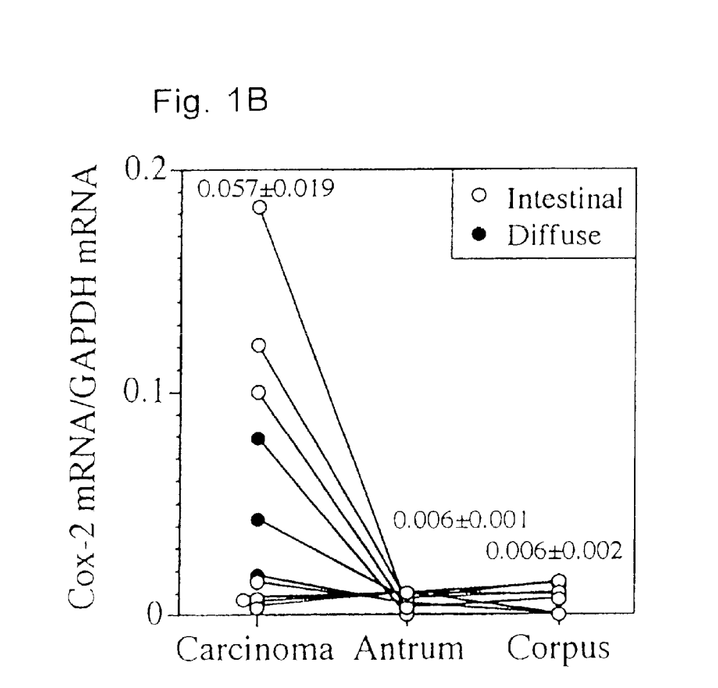
FIG. 1B. Ratio of Cox-2 mRNA to GAPDH mRNA is shown. Values (means±SEM) in the graphs represent the ratio of Cox-2 mRNA to GAPDH mRNA calculated from the arbitrary densitometric units, which indicate that gastric carcinoma tissues expressed significantly higher levels of Cox-2 mRNA than did the control samples ($P<0.05$).

Gastric carcinoma tissues expressed significantly higher levels of Cox-2 mRNA than did antrum or corpus samples, which were devoid of cancer cells, as detected by Northern blot hybridization (FIG. 1A). The Cox-2 transcripts were expressed both by intestinal and diffuse adenocarcinomas. Levels of Cox-2 mRNA did not correlate with the proportion of carcinoma tissue in the specimens. FIG. 1B shows that gastric carcinoma tissues expressed significantly higher levels of Cox-2 mRNA than did the control samples (P<0.05).

Figure 1C:
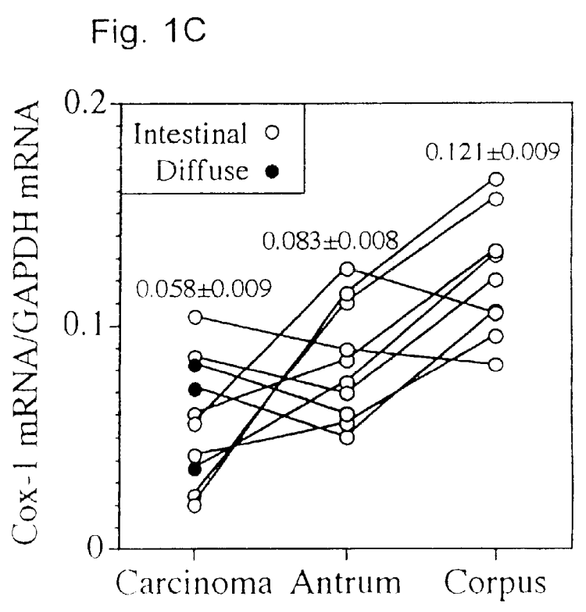
FIG. 1C. Ratio of Cox-1 mRNA to GAPDH mRNA is shown. Values (means±SEM) in the graphs represent the ratio of Cox-1 mRNA to GAPDH mRNA calculated from the arbitrary densitometric units. Cox-1 mRNA levels were not elevated in the carcinoma tissues.

As shown in FIG. 1C, levels of Cox-1 transcripts were not elevated in the carcinoma tissues, when compared to the levels in their respective controls.

Figure 2:
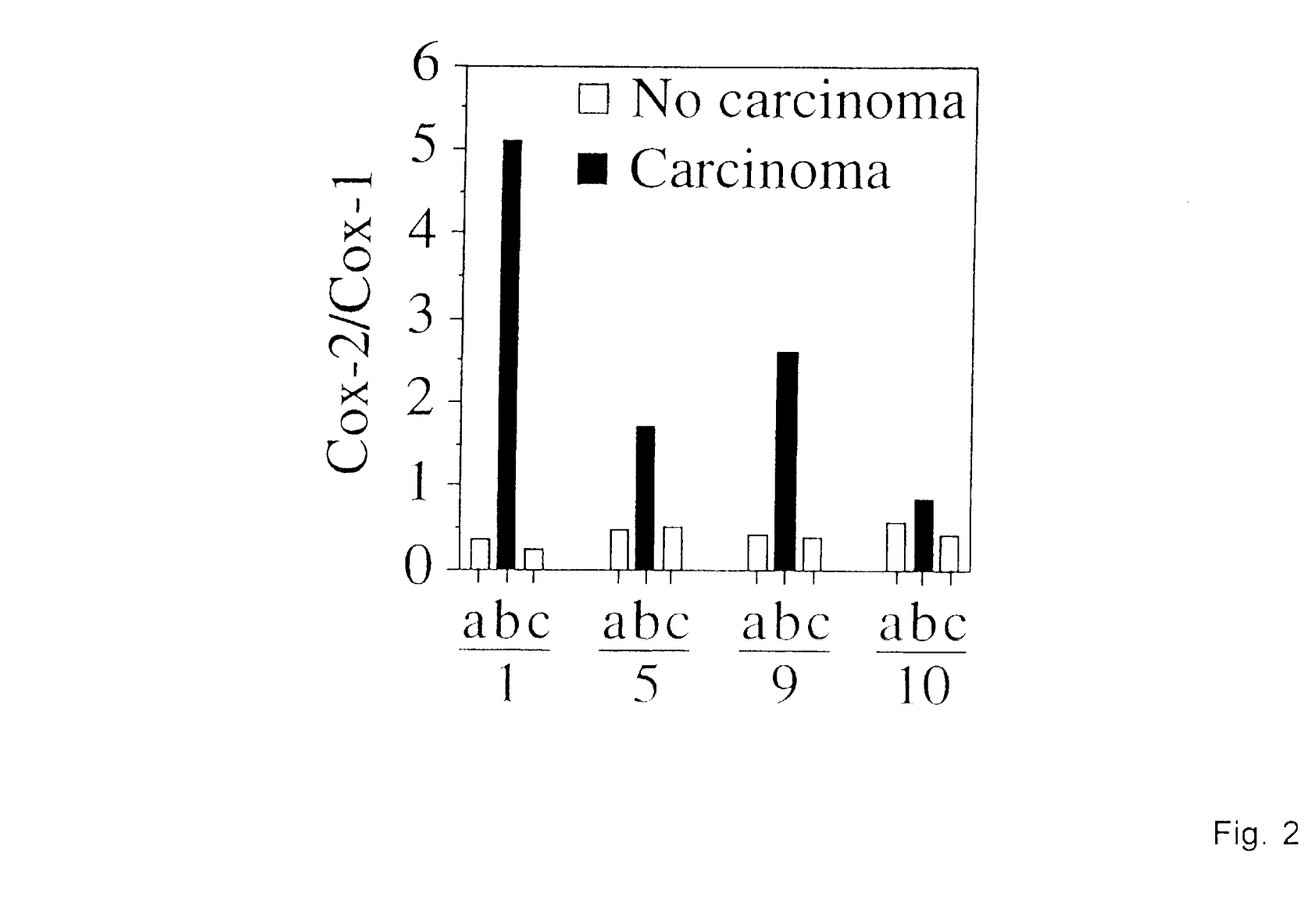
FIG. 2. Cox-1 and Cox-2 mRNA levels were detected by RT-PCR in gastric carcinoma specimens (identified as b) of the cases 1, 5, 9, and 10 and from their respective controls that were devoid of cancer cells (a, antrum; c, corpus). Total RNA was first reverse transcribed. Then the cDNA samples were amplified with PCR using isoenzyme specific primers for human Cox-1 and Cox-2. Finally, the PCR products were analyzed and quantitated (see Experimental). Graph shows ratio of Cox-2 mRNA to Cox-1 mRNA.

Three gastric carcinoma samples (numbers 5, 9, 10) expressed low levels of Cox-2 mRNA as detected by the Northern blot assay (FIG. 1A). To further evaluate the level of Cox-1 and Cox-2 expression in these samples, we performed a semi-quantitative RT-PCR, with sample number 1 as a positive control. As shown in FIG. 2, the ratio of Cox-2 mRNA to Cox-1 mRNA was higher in carcinoma samples than in paired antrum or corpus samples that contained no cancer cells.

Figure 3A:
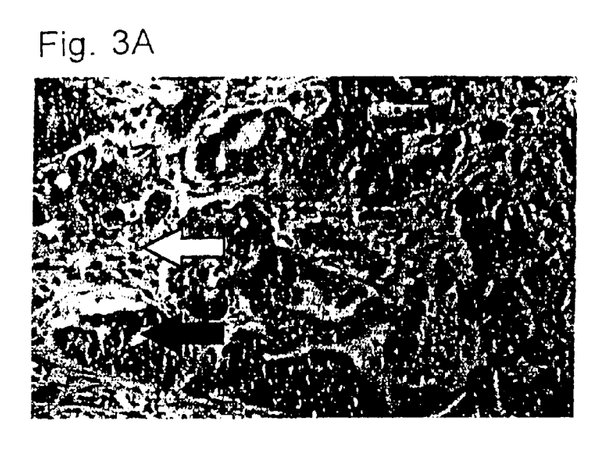
FIG. 3A. Immunohistological staining for Cox-2 in gastric carcinoma tissues showed cytoplasmic staining (red-brown color) in the cancer cells (black arrow), but not in the surrounding stroma (white arrow).
Figure 3B:
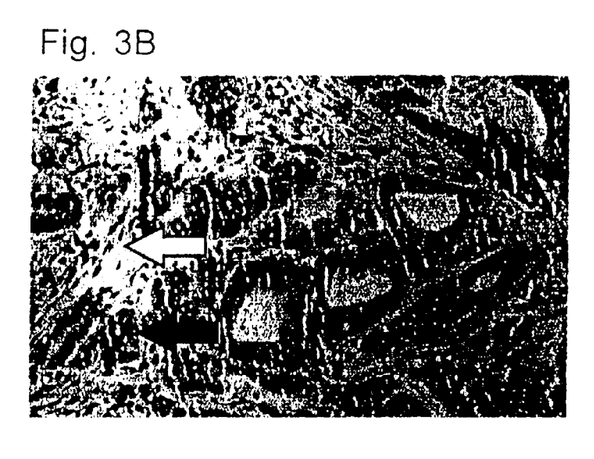
FIG. 3B. When normal rabbit IgG was used as the primary antibody, tissue sections exhibited no staining.
Figure 3C:
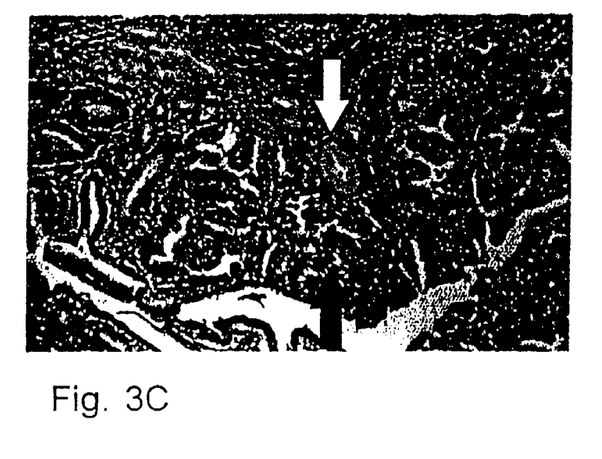
FIG. 3C and FIG. 3D. Grave gastric dysplasia specimens from two separate patients were stained with the Cox-2 antibodies. Dysplastic glands (black arrows) were positive for Cox-2, whereas normal glands (white arrows) were negative.
Figure 3D:
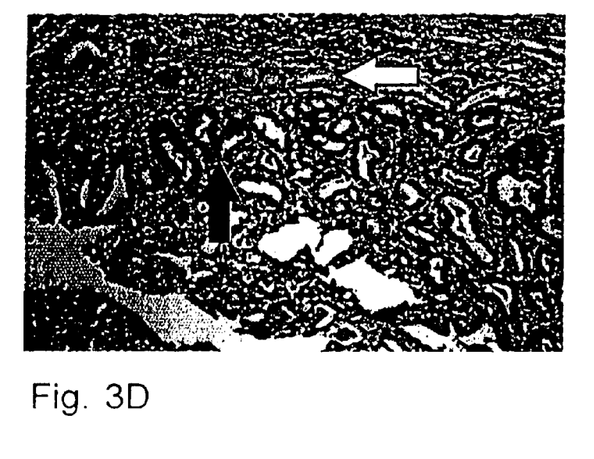

As shown in FIG. 3A, immunohistological staining with Cox-2 specific polyclonal antibodies showed cytoplasmic staining in the cancer cells (black arrow), but not in the surrounding stroma (white arrow). When normal rabbit IgG was used as primary antibody, tissue sections exhibited no staining (FIG. 3B). Importantly, FIGS. 3C and 3D show that grave gastric dysplasia specimens from two separate patients were stained with the Cox-2 antibodies. Dysplastic glands (black arrows) were positive for Cox-2, whereas normal glands (white arrows) were negative. The normal rabbit IgG did not show positive staining (not shown).

REFERENCES

Antonioli, D. A. Precursors of gastric carcinoma: a critical review with a brief description of early (curable) gastric cancer. Hum. Pathol., 25: 994–1005, 1994.

Chomczynski, P., and Sacchi, N. Single-step method of RNA isolation by acid guadinium thiocyanate-phenol-chloroform extraction. Anal. Biochem., 162: 156–159, 1987.

Coleman, M. P., Esteve, J., Damiecki, P., Arslan, A., and Renard, H. Trends in cancer incidence and mortality. In: IARC Scientific Publications No. 121, pp. 193–224. Lyon, 1993.

DuBois, R. N., Radhika, A., Reddy, B. S., and Entingh, A. J. Increased cyclooxygenase-2 levels in carcinogen-induced rat colonic tumors. Gastroenterology, 110: 1259–1262, 1996.

Eberhart, C. E., Coffey, R. J., Radhika, A., Giardiello, F. M., Ferrenbach, S., and DuBois, R. N. Up-regulation of cyclooxygenase 2 gene expression in human colorectal adenomas and adenocarcinomas. Gastroenterology, 107: 1183–1188, 1994.

Giardiello, F. M. Sulindac and polyp regression. Cancer Metastasis Rev., 13: 279–283, 1994.

Giardiello, F. M., Offerhaus, G. J. A., and DuBois R. N. The role of nonsteroidal anti-inflammatory drugs in colorectal cancer prevention. Eur. J. Cancer, 31A: 1071–1076, 1995.

Herschman, H. R. Prostaglandin synthase 2. Biochim. Biophys. Acta, 1299: 125–140, 1996.

Kargman, S. L., O'Neill, G. P., Vickers, P. J., Evans, J. F., Mancini, J. A., and Jothy, S. Expression of prostaglandin G/H synthase-1 and -2 protein in human colon cancer. Cancer Res., 55: 2556–2559, 1995.

Kargman, S., Charleson, S., Cartwright, M., Frank, J., Riendeau, D., Mancini, J., Evans, J., and O'Neill, G. Characterization of prostaglandin G/H synthase 1 and 2 in rat, dog, monkey, and human gastrointestinal tracts. Gastroenterology, 111: 445–454, 1996.

Laakso, M., Mutru, O., Isomäki, H., and Koota, K. Cancer mortality in patients with rheumatoid arthritis. J. Rheumatol., 13: 522–526, 1986.

Laurén, P. The two histological main types of gastric carcinoma: diffuse and so-called intestinal-type carcinomas: an attempt at a histo-clinical classification. Acta Path. Microbiol. Scandinav., 64: 31–49, 1965.

O'Neill, G. P., and Ford-Hutchinson, A. W. Expression of mRNA for cyclooxygenase-1 and cyclooxygenase-2 in human tissues. Febs Lett., 330: 156–160, 1993.

Oshima, M., Dinchuk, J. E., Kargman, S. L., Oshima, H., Hancock, B., Kwong, E., Trzaskos, J. M., Evans, J. F., and Taketo, M. M. Suppression of intestinal polyposis in Apc716 knockout mice by inhibition of cyclooxygenase 2 (Cox-2). Cell, 87: 803–809, 1996.

Reddy, B. S., Rao, C. V., and Seibert, K. Evaluation of cyclooxygenase-2 inhibitor for potential chemopreventive properties in colon carcinogenesis. Cancer Res., 56: 4566–4569, 1996.

Ristimäki, A., Garfinkel, S., Wessendorf, J., Maciag, T., Hla, T. Induction of cyclooxygenase-2 by interleukin-1α. Evidence for post-transcriptional regulation. J. Biol. Chem., 269: 11769–11775, 1994.

Sano, H., Kawahito, Y., Wilder, R. L., Hashiramoto, A., Mukai, S., Asai, K., Kimura, S., Kato, H., Kondo, M., and Hla, T. Expression of cyclooxygenase-1 and -2 in human colorectal cancer. Cancer. Res., 55: 3785–3789, 1995.

Sheng, H., Shao, J., Kirkland, S. C., Isakson, P., Coffey, R. J., Morrow, J., Beauchamp, R. D. and Dubois, R. N. Inhibition of human colorectal cancer cell growth by selective inhibition of cyclooxygenase-2. J. Clin. Invest., 99: 2254–2259, 1997.

Smith, W. L., Garavito, R. M., and DeWitt, D. L. Prostaglandin endoperoxide H synthases (cyclooxygenases)-1 and -2. J. Biol. Chem., 271: 33157–33160, 1996.

Steele, V. E., Moon, R. C., Lubet, R. A., Grubbs, C. J., Reddy, B. S,. Wargovich, M., McCormick, D. L., Pereira, M. A., Crowell, J. A., Bagheri, D., Sigman, C. C., Boone, C. W., and Kelloff, G. J. Preclinical efficacy evaluation of potential chemopreventive agents in animal carcinogenesis models: methods and results from the NCI Chemoprevention Drug Development Program. J. Cell. Biochem. Suppl., 20: 32–54, 1994.

Stemmermann, G., Heffelfinger, S. C., Noffsinger, A., Hui, Y. Z., Miller, M. A., and Fenoglio-Preiser, C. M. The molecular biology of esophageal and gastric cancer and their precursors: oncogenes, tumor suppressor genes, and growth factors. Hum. Pathol., 25: 968–981, 1994.

Subbaramaiah, K., Telang N., Ramonetti, J. T., Araki, R. DeVito, B., Weksler, B. B. and Dannenberg, A. J. Transcription of cyclooxygenase-2 is enhanced in transformed mammary epithelial cells. Cancer Res., 56: 4424–4429, 1996.

Tahara, E., Semba, S., and Tahara, H. Molecular biological observations in gastric cancer. Semin. Oncol., 23: 307–315, 1996.

Takahashi, M., Fukutake, M., Yokota, S., Ishida, K., Wakabayashi, K., and Sugimura, T. Suppression of azoxymethaneinduced aberrant crypt foci in rat colon by nimesulide, a selective inhibitor of cyclooxygenase 2. J. Cancer Res. Clin. Oncol., 122: 219–222, 1996.

Thun, M. J. Aspirin, NSAIDs, and digestive tract cancers. Cancer Metastasis Rev., 13: 269–277, 1994.

Thun, M. J., Namboodiri, M. M., Calle, E. E., Flanders, W. D., and Heath Jr., C. W. Aspirin use and risk of fatal cancer. Cancer Res., 53: 1322–1327, 1993.

Tsuji, S., Kawano, S., Sawaoka, H., Takei, Y., Kobayashi, I., Nagano, K., Fusamoto, H. and Kamada, T. Evidences for involvement of cyclooxygenase-2 in proliferation of two gastrointestinal cancer cell lines. Prostagland. Leuk. Essent. Fatty., 55: 179–183, 1996.

Tsujii, M., and DuBois, R. N. Alterations in cellular adhesion and apoptosis in epithelial cells overexpressing prostaglandin endoperoxide synthase 2. Cell, 83: 493–501, 1995.

Wanebo, H. J., Kennedy, B. J., Chmiel, J., Steele, G. J., Winchester, D., and Osteen, R. Cancer of the stomach. A patient care study by the American College of Surgeons. Ann. Surg., 218: 583–592, 1993.

What is claimed is:

1. A method for determination of the significance of a histologically detected premalignant lesion as a risk for intestinal type gastric cancer or carcinoma in situ, comprising detecting from a patient sample comprising gastric mucosa cells a) cyclooxygenase-2 (Cox-2) mRNA expression, or b) Cox-2 protein;

wherein overexpression of Cox-2 is indicative of an increased risk for intestinal type gastric cancer.

2. The method according to claim 1, wherein the patient sample to be detected is a biopsy or a brush sample.

3. The method according to claim 1, wherein detection of Cox-2 mRNA expression is carried out using Northern Blot, in situ hybridization, RNase protection, or RT-PCR based techniques, or a combination thereof.

4. The method according to claim 1, wherein detection of Cox-2 protein is carried out using poly- or monoclonal antibodies wherein said antibodies bind specifically to Cox-2 protein, or immunohistochemistry.

5. The method according to claim 3, wherein said method is carried out using a kit comprising RNA or polyA+mRNA isolation reagents, Cox-2 specific primers for RT-PCR and Cox-2 specific cDNA fragments for making either DNA or RNA probes.

6. The method according to claim 4, wherein said method is carried out using a kit comprising Cox-2 specific polyclonal or monoclonal antibodies.

7. A method for detecting intestinal type gastric carcinoma at a premalignant phase, comprising the steps of:

providing a gastric mucosa cell sample from said patient, and detecting Cox-2 mRNA expression or Cox-2 protein in said sample, wherein overexpression of Cox-2 is indicative of an increased risk for intestinal type gastric cancer.

* * * * *